United States Patent
Parman et al.

(10) Patent No.: US 9,456,979 B2
(45) Date of Patent: Oct. 4, 2016

(54) ADMINSTRATION OF INTACT MAMMALIAN CELLS TO THE BRAIN BY THE INTRANASAL ROUTE

(75) Inventors: Toufan Parman, Foster City, CA (US); Rebecca Erickson, Brisbane, CA (US); Karen Steinmetz, Pacifica, CA (US)

(73) Assignee: SRI INTERNATIONAL, Menlo Park, CA (US)

( * ) Notice: Subject to any disclaimer, the term of this patent is extended or adjusted under 35 U.S.C. 154(b) by 2195 days.

(21) Appl. No.: 11/796,631

(22) Filed: Apr. 27, 2007

(65) Prior Publication Data

US 2008/0260699 A1    Oct. 23, 2008

Related U.S. Application Data

(60) Provisional application No. 60/745,802, filed on Apr. 27, 2006.

(51) Int. Cl.
| | |
|---|---|
| *A61K 35/12* | (2015.01) |
| *A61P 25/00* | (2006.01) |
| *A61K 9/00* | (2006.01) |
| *C12N 5/0797* | (2010.01) |

(52) U.S. Cl.
CPC .......... *A61K 9/0043* (2013.01); *C12N 5/0623* (2013.01); *A61K 35/12* (2013.01)

(58) Field of Classification Search
None
See application file for complete search history.

(56) References Cited

U.S. PATENT DOCUMENTS

2005/0032209 A1 *  2/2005  Messina et al. .............. 435/366

OTHER PUBLICATIONS

Clarisa M. Buckner et al. "Neuroimmunity and the Blood-Brain Barrier: Molecular Regulation of Leukocyte Transmigration and Viral Entry into the Nervous System with a Focus on NeuroAIDS" J Neuroimmune Pharmacol (2006) 1: 160-181.*
Jack Aurora "Development of Nasal Delivery Systems: A Review" Drug Delivery Technologies vol. 2 No. 7 Oct. 2002.*
Alla L. Zozulya et al. "Dendritic Cell Transmigration MIP-1{alpha} Chemokine and Matrix Metalloproteinases" J. Immunol. 2007;178;520-529.*
Sergio M. Gloor et al. "Molecular and cellular permeability control at the blood-brain barrier" Brain Research Reviews 36 (2001) 258-264.*
Xavier Nassif et al. "How do extracellular pathogens cross the blood-brain barrier?" Trends in Microbiology vol. 10 No. 5 May 2002.*
O. Dale et al. "Nasal administration of opioids for pain management in adults" Acta Anaesthesiol Scand 2002; 46: 759-770.*
R. G. Thorne, G. J. Pronk, V. Padmanabhan and W. H. Frey II, Delivery of Insulin-Like Growth Factor-I to the Rat Brain and Spinal Cord Along Olfactory and Trigeminal Pathways Following Intranasal Administration, 2004, Neuroscience, vol. 127, pp. 481-496.*
Stephen C. Noctor, Alexander C. Flint, Tamily A. Weissman, Winston S. Wong, Brian K. Clinton, and Arnold R. Kriegstein, Dividing Precursor Cells of the Embryonic Cortical Ventricular Zone Have Morphological and Molecular Characteristics of Radial Glia, 2002, J. Neurosci., 22(8):3161-3173.*
Y. Ogawa, K. Sawamoto, T. Miyata, S. Miyao, M. Watanabe, M. Nakamura, B.S. Bregman, M. Koike, Y. Uchiyama, Y. Toyama, and H. Okano, Transplantation of in Vitro-Expanded Fetal Neural Progenitor Cells Results in Neurogenesis and Functional Recovery After Spinal Cord Contusion Injury in Adult Rats, 2002, Journal of Neuroscience Research 69:925-933.*
Lusine Danielyan, Richard Schafer, Andreas von Ameln-Mayerhofer, Marine Buadze, Julia Geisler, Tim Klopfer, Ute Burkhardt, Barbara Proksch, Stephan Verleysdonk, Miriam Ayturan, Gayane H.Buniatian, Christoph H.Gleiter, William H. Frey II , Intranasal delivery of cells to the brain , 2009, European Journal of Cell Biology, vol. 88, pp. 315-324.*

* cited by examiner

*Primary Examiner* — Ralph Gitomer
*Assistant Examiner* — Trent Clark
(74) *Attorney, Agent, or Firm* — Richard Aron Osman

(57) ABSTRACT

The present invention provides an intranasal method for delivery of intact mammalian cells to the brain for treatment of neurological deficits. This approach applies an intranasal instillation to directly administer cells to the brain, and is useful as therapy for patients with neurological deficit or those who may benefit from cellular therapy as a result of stroke, Alzheimer's, Parkinson's, diabetes, traumatic injury, surgery, cancer, or other diseases of the brain. This non-invasive method of delivering neuronal cells is desirable and safe.

19 Claims, No Drawings

ADMINSTRATION OF INTACT MAMMALIAN CELLS TO THE BRAIN BY THE INTRANASAL ROUTE

CROSS-REFERENCE TO RELATED APPLICATIONS

This application claims priority from U.S. Provisional Patent Application No. 60/745,802, filed Apr. 27, 2006, which is incorporated herein by reference.

FIELD OF THE INVENTION

The present invention relates generally to medicine. More particularly, the present invention relates to administration of intact mammalian cells to the brain by the intranasal route.

BACKGROUND

Growing evidence suggests that neural transplant and stem cell therapies may benefit patients with neurodegenerative conditions such as traumatic brain injury, Alzheimer's and Parkinson's disease. Methods to deliver cells to the brain that bypass the blood brain barrier include intrathecal or intracranial routes, both of which are costly, invasive, and may lead to further damage. Therefore, the blood brain barrier presents a significant drawback for non-invasive delivery of cells into the brain. However, to date, a non-invasive method for delivery of stem cells to the brain has not been described. Accordingly, there is a need in the art to develop non-invasive methods for administering live whole intact mammalian cells to the brain.

SUMMARY OF THE INVENTION

The present invention provides delivery of whole mammalian cells into the brain. In a preferred embodiment, the delivery is intranasal. In other preferred embodiments, the mammalian cells may be stem cells (i.e., totipotent or pluripotent), progenitor cells (i.e., multipotent), genetically modified cells (e.g. gene therapy), established cell lines (e.g. immortalized cells), and/or other relevant or useful cell types (e.g. cells that are able produce and secrete specific antibodies).

The present invention also provides improved methods for treatment of neurological disease, including intranasal delivery of intact mammalian cells to sites of damage within the brain.

The present invention further provides methods for intranasal delivery of autologously-derived intact cells, i.e., obtained from the host, to the brain of the same host. The cells may be genetically modified to control their proliferation and/or to introduce modulators for therapeutic purposes.

The present invention further provides methods for guiding the migration of cells that are delivered via the intranasal route into the brain to specific brain or other central nervous system sites.

DETAILED DESCRIPTION OF THE INVENTION

The present invention provides an intranasal method for delivery of live intact mammalian cells for treatment of neurological deficits to specific sites of damage within the brain. This approach applies an intranasal instillation to directly administer cells to the brain and is useful as therapy for patients with neurological deficit or those in need of neural therapy such as patients with stroke, Alzheimer's or Parkinson's disease, diabetes, traumatic injury, surgery, cancer, or other cerebral damage or diseases of the brain. This non-invasive method of delivering intact cells is desirable and safe.

Various methods of intranasal dose administration may be used to deliver cells to the upper third of the nasal cavity. Delivery devices may include (1) liquid nasal spray, (2) nose drops, (3) ointment, (4) pledget, (5) submucosal infusion, and/or (6) mucoadhesive strips. Delivery medium, comprising one or more of the following: TB, FS, and/or intact neural progenitors, may include (1) neurobasal medium, (2) phosphate-buffered saline, and (3) gels (e.g. matrigel). Other devices/medium may be used if these methods are found not to be optimal for cell delivery.

To test the efficacy of a particular delivery protocol, cells may be delivered in Neurobasal medium (NBM), used as a vehicle; Neurobasal medium plus toluidine blue; Neurobasal medium plus toluidine blue plus Fluospheres® aldehyde-sulfate microspheres, 0.02 µm, (505/515λ) (FS$^1$); or Neurobasal medium plus toluidine blue plus Fluospheres® aldehyde-sulfate microspheres, 1.0 µm, (580/605λ) (FS$^2$) in a delivery volume of 50l. While 50 µl is stated here, this volume may be varied depending on experimental observations and outcomes. Rats may then be sacrificed 4 hours, 24 hours, 7 days, or 14 days after delivery to determine a) the location and extent of dispersal of tracers such as toluidine blue (TB) and/or FluoSpheres (FS) within the nasal cavity and/or whole brain, b) the point of entry along the olfactory epithelium/cribiform plate, and c) the best delivery device or method to achieve optimal delivery to the brain.

Any concentration of cells may be administered according to the present method. Preferably, cell concentration ranges from about 10 to about 10,000 cells/µl. In addition, cells may take any time course to migrate into the brain, but preferably take from about 4 hours to about two weeks. To determine a) the optimal concentration of cells for delivery, and (b) a time course of entry into the brain, the experimental parameters shown in Table 1 may be used. However, these parameters may be varied based on experimental observations and outcomes.

TABLE I

Intranasal Delivery of Green Florescent Protein (GFP) Expressing Neural Progenitor Cells to Rats

| Group | Dose Level Cells/µl | Number of Cells | Delivery Volume (µl) | Time of Sacrifice/Necropsy (n) | | | |
|---|---|---|---|---|---|---|---|
| | | | | 4 hr | 24 hr | 7 d | 14 d |
| 1 | NBM | 0 | 50 | 3 | 3 | 3 | 3 |
| 2 | NBM + FS$^1$ + FS$^2$ | 0 | 50 | 3 | 3 | 3 | 3 |
| 3 | 10 | 500 | 50 | 3 | 3 | 3 | 3 |
| 4 | 40 | 2000 | 50 | 3 | 3 | 3 | 3 |
| 5 | 200 | 10,000 | 50 | 3 | 3 | 3 | 3 |
| 6 | 1,000 | 50,000 | 50 | 3 | 3 | 3 | 3 |
| 7 | 10,000 | 500,000 | 50 | 3 | 3 | 3 | 3 |

Cells of any origin may be used for delivery according to the present invention. For example, cells may be stem cells of restricted (i.e., multipotent) or unlimited (i.e., totipotent/ or pluripotent) potential. Cells may be pre-differentiated with agents in culture or restricted neuronal cell lines (e.g., PC12 cell line). Cells may be of tumorigenic origin. Cells may also be of non-neuronal origin.

Cells may also be modified prior to delivery. Specific genes in stem cells may be manipulated to increase differentiation of specific neuronal subtypes (e.g., dopaminergic neurons); these may include but are not limited to SHH, Wnt1, FGF8, Nodal, Fox2a, En1/2, Lmx1a/b, Wnt5a, FGF20, Slt2, Robo1/2, Neutrin1, GDNF, Nurr1, and/or Ngn2. Cells may be manipulated by chemical or other suitable proliferative or differentiation agents or by genetic modification. Alternatively, or in addition, cells may be modified to produce and secrete specific antibodies, such as those used in treating brain cancers.

Subjects may be treated before, during or after, delivery of cells according to the present invention with various cytokines, chemokines, and/or growth factors via intranasal, oral, intravenous, transdermal, intradermal, ocular, or subcutaneous routes. This treatment may increase the efficiency of entry and migration of cells delivered via the intranasal route. Cytokines may include but are not limited to interleukins (IL), tissue necrosis factors (TNF), interferons and tissue growth factors (TGF). Chemokines may include but are not limited to those that can bind CXC, CC and other chemokine receptors. Other growth factors may include but are not limited to NGF, GDNF, BDNF, IGF-1, insulin, EGF, and/or FGFs.

Subjects may also, or alternatively, be treated before, during or after, delivery of cells according to the present invention with various immunosuppressants (e.g., cyclosporine) or immunoenhancers (e.g., interferons, antioxidants) to manipulate the immune system. Activated immune cells of the mucosal lining may impede the entry of foreign material (including non-autologous cells) into the brain via the intranasal route. Thus, manipulating the immune system may increase the efficiency of cell delivery according to the present invention.

Modulation and/or disruption of mucus may also be used to enhance delivery of the cells to the brain. Therefore, subjects may also, or alternatively, be pretreated with mucus removing agent(s) to reduce mucal secretions. This may include but not be limited to use of glycosidases, decongestant, etc. to remove or reduce mucus density/thickness in the delivery area (upper third of the nasal cavity).

Injury is known to result in release of chemotactic signaling factors that direct the movement of cells to the site of injury. Therefore, brains of subjects may be injured to mimic trauma. Examples of brain injury include MPTP-induced degeneration of dopaminergic neurons, middle cerebral artery occlusion, or the use of other animal models of neurodegenerative diseases (e.g., stroke, Alzheimer's, Parkinson's and Huntington's Diseases).

EXAMPLES

A. Preparation of GFP Neurospheres for Delivery

In one embodiment, these steps may be followed: timed-pregnant transgenic Sprague-Dawley dams expressing GFP [such as but not limited to (SD-Tg(GFP)2BalRrrc), Rat Resource and Research Center (RRRC)] may be ordered to arrive at least 3 weeks prior to the scheduled intranasal delivery procedures. Within 24 hours of delivery, pups may be decapitated and whole brains may be removed and placed into individual Petri dishes containing cold (4° C.) Hanks Balanced calcium/magnesium free Saline Solution (HBSS). The neocortex may be dissected, including the lateral subventricular zones which contain cell progenitors, and placed into tubes containing HBSS. After removal of vascular meninges, tissue may be mechanically dissociated and resuspended in Neurobasal media. Cell suspensions may be centrifuged at 1000 RPM (205 RCF) for 5 min and resuspended into fresh neurosphere-growing medium (see below). Live cells may be determined by Trypan blue exclusion, counted and seeded at 50 cells per microliter (cpµL) in 25 cm tissue-culture-treated flasks.

After six days in culture, GFP+ neurospheres may be transfected with FluoSpheres (FS; Invitrogen, 0.2 µm, red fluorescent-labeled). The procedure may be adopted from the published methods in the literature.

One day after transfection, neurospheres may be prepared for transplantation. Neurospheres may be transferred to 50 ml centrifuge tubes, centrifuged at 800 RPM (150 RCF) for 5 minutes, and the old media may be removed. Neurospheres may be dissociated into a single-cell suspension using both chemical and mechanical means: 5 ml 0.05% Trypsin-EDTA along with the assistance from a small-bore (100-200 µm), fire-polished glass pipette. Following dissociation, Trypsin-EDTA may be diluted 1:1 with fresh neurosphere medium. Cell suspensions may be centrifuged at 1200 RPM (340 RCF) for 5 minutes, washed once in neurosphere medium, and then transferred through a 40 µm cell strainer to obtain a single cell suspension. The live cell concentration may be determined with trypan blue exclusion and then re-seeded into neurobasal medium at the appropriate concentrations to obtain the required dose levels. Cells may be kept on ice and then brought to room temperature prior to administration.

Neurosphere media: Neurobasal media, B-27 (1:50), L-glutamine (2 mM), epidermal growth factor (EGF; 10 ng/ml), fibroblast growth factor-2 (FGF2, human recombinant; 20 ng/ml), heparin (2 ug/ml), and Penicillin/Streptomycin (1:100). Medium is preferably supplemented with both EGF and FGF2 every third day.

B. Intranasal Delivery and Post-Operation Methods

In one embodiment, the following steps may be followed: Rats may be anesthetized and placed in a supine position with a pad inserted under the dorsal neck to extend the head back toward the supporting surface. Using the device/medium for delivery, an average of 50 µl total medium (with or without cells) may be delivered intranasally by adding 6-8 µl drops alternatively to each naris every 2-3 min over a total of 20 minutes. Rats may then be returned to their respective home cages and observed until full recovery from anesthesia is regained.

C. In-Life Evaluations

Dose administration (Day 1) may be followed by animal sacrifice/necropsy at the following timepoints: 4 hr, 24 hr, 7 d, and 14 d. Within 1 hr post-dose and daily thereafter during in-life, animals may be observed daily for mortality/morbidity and routine clinical observations. Bodyweights may be taken on Days 1, 7 and 14.

D. Tissue Preparation

To determine the optimal delivery method, at the time of sacrifice/necropsy, rats may be deeply anesthetized with an overdose of sodium pentobarbital (~150 mpk i.p.) then decapitated according to SRI's SOP. Rats will not be perfused in an effort to detect possible entry of TB and/or FS into the vascular system surrounding the brain. Whole brains may be removed from the skulls and both the brain and skull may be preserved in 10% formalin until sectioning. For sectioning of whole brains, the tissue may be cut rostral to caudal. From the olfactory bulb through the mid-cerebrum at the optic chiasm, every section may be saved.

From the optic chiasm through the cranial cervical cord, every 4$^{th}$ section may be saved. Some brain slices may be stained with hematoxylin and eosin (H&E) to determine the histostructures. All slides will be protected from light until microscopic analyses are to be done. For sectioning of the skull, rostral to caudal sections may be cut at 20 μm thick (or the thinnest possible) consecutive intervals throughout the entirety of the nasal conchae—approximately 1000 sections totaling 2 cm.

In addition, stomach and lung tissue may be necropsied. Stomach epithelial lining and bronchial tissue may be sectioned to determine whether TB and/or FS have entered these cavities.

For determining the ideal cell concentration and time course of migration, perfusion techniques will be used post-anesthesia in order to optimize tissue fixation and to determine that cells and FS are within the brain tissue and not the surrounding, vacular system. At the time of sacrifice/necropsy, rats may be deeply anesthetized with an overdose of sodium pentobarbital (~150 mpk i.p.). When the rat is non-responsive by paw pinch and forcep touch to eye, the thoracic cavity may be opened and the heart exposed. Following injection of cold PBS (pH 7.4) into the left ventricle, the right atrium may be pierced to allow efflux of blood. A stopcock may be engaged to switch the perfusion medium to 50 ml cold 1.5% paraformaldehyde (pH 7.4). Whole brain and skull sections may be prepared as described above. Stomach epithelial lining and bronchial tissue may be sectioned to determine whether FS and/or cells have entered these cavities.

E. Determining Entry of Toluidine Blue, FluoSpheres, and Neural Progenitors

Fluorescence microscopy may be used to determine the permeation of intranasally-delivered preparations into the brain. Sections from both whole heads and whole brains may be analyzed from rostral to caudal ends, identifying TB dye, FS-positivity (515λ, 605λ), and/or GFP-positivity (509λ) using a dual-pass excitation filter set under a fluorescent microscope. For example, a 20× objective lens and a dual-pass FITC-UV filter may be used. Distance between entry point (olfactory epithelium along cribiform plate) and olfactory bulb/other may be estimated based on knowledge of slide number and section thickness. An estimation of efficiency rate (e.g., percentage of cells entering brain from total delivered) may be determined.

As one of ordinary skill in the art will appreciate, various changes, substitutions, and alterations could be made or otherwise implemented without departing from the principles of the present invention. Accordingly, the scope of the invention should be determined by the following claims and their legal equivalents.

What is claimed is:

1. A method for delivering intact mammalian cells to the brain of a mammal, comprising administering intranasally to a rat a suspension of viable rat neural progenitor cells, whereby the cells bypass the blood-brain-barrier and enter the brain of the rat, wherein the suspension is administered in nose drops to a naris of the rat.

2. The method of claim 1 wherein the suspension has 10-10,000 cells/ul.

3. The method of claim 1 wherein the suspension has 10,000 cells/ul.

4. The method of claim 1 wherein the suspension has 10-10,000 cells/ul and is 50 ul.

5. The method of claim 1 wherein the suspension has 10,000 cells/ul and is 50 ul.

6. The method of claim 1 wherein the suspension is administered in a liquid nasal spray, nose drops, ointment, pledget, submucosal infusion or mucoadhesive strip.

7. The method of claim 1 wherein the cells are suspended in neurobasal medium, phosphate-buffered saline or gel.

8. The method of claim 1 wherein the cells are suspended in neurobasal medium.

9. The method of claim 1, wherein the suspension is administered 6-8 ul to each naris of the rat every 2-3 min over a total of 20 min.

10. The method of claim 1, wherein the cells are labeled with GFP.

11. The method of claim 1, wherein the cells are labeled with fluorospheres.

12. The method of claim 1, further comprising the step of detecting the cells in the brain of the rat.

13. The method of claim 1 wherein the suspension has 10-10,000 cells/ul, the cells are suspended in neurobasal medium and the suspension is administered 6-8 ul to each naris of the rat every 2-3 min over a total of 20 min, further comprising the step of detecting the cells in the brain of the rat.

14. A method for delivering intact mammalian cells to the brain of a mammal, comprising administering intranasally and non-invasively by nose drops to a naris of a rat a suspension of viable rat neural progenitor cells, whereby the cells bypass the blood-brain-barrier and enter the brain of the rat.

15. The method of claim 14 wherein the suspension has 10-10,000 cells/ul.

16. The method of claim 14 wherein the cells are suspended in neurobasal medium, phosphate-buffered saline or gel.

17. The method of claim 14, wherein the suspension is administered 6-8 ul to each naris of the rat every 2-3 min over a total of 20 min.

18. The method of claim 14 further comprising the step of detecting the cells in the brain of the rat.

19. The method of claim 14 wherein the suspension has 10-10,000 cells/ul, the cells are suspended in neurobasal medium and the suspension is administered 6-8 ul to each naris of the rat every 2-3 min over a total of 20 min, further comprising the step of detecting the cells in the brain of the rat.

* * * * *